US010093749B2

(12) United States Patent
Yamamoto et al.

(10) Patent No.: US 10,093,749 B2
(45) Date of Patent: Oct. 9, 2018

(54) EXOPOLYSACCHARIDE PRODUCED BY LACTIC ACID BACTERIUM

(71) Applicant: NITTO PHARMACEUTICAL INDUSTRIES, LTD., Muko-shi, Kyoto (JP)

(72) Inventors: Kenji Yamamoto, Otsu (JP); Chiaki Matsuzaki, Kanazawa (JP); Keiko Hisa, Muko (JP)

(73) Assignee: NITTO PHARMACEUTICAL INDUSTRIES, LTD., Muko (JP)

( * ) Notice: Subject to any disclaimer, the term of this patent is extended or adjusted under 35 U.S.C. 154(b) by 68 days.

(21) Appl. No.: 15/023,013

(22) PCT Filed: Sep. 18, 2014

(86) PCT No.: PCT/JP2014/074725
§ 371 (c)(1),
(2) Date: Mar. 18, 2016

(87) PCT Pub. No.: WO2015/041299
PCT Pub. Date: Mar. 26, 2015

(65) Prior Publication Data
US 2016/0229925 A1 Aug. 11, 2016

(30) Foreign Application Priority Data

Sep. 19, 2013 (JP) ................................. 2013-194656

(51) Int. Cl.
| | | |
|---|---|---|
| *C08B 37/00* | (2006.01) | |
| *A23K 20/163* | (2016.01) | |
| *A61K 31/715* | (2006.01) | |
| *A61K 8/73* | (2006.01) | |
| *A61Q 19/00* | (2006.01) | |
| *C12P 19/04* | (2006.01) | |
| *A23L 29/269* | (2016.01) | |
| *A23L 33/135* | (2016.01) | |
| *A23L 33/10* | (2016.01) | |
| *A61K 35/74* | (2015.01) | |

(52) U.S. Cl.
CPC ............ *C08B 37/00* (2013.01); *A23K 20/163* (2016.05); *A23L 29/273* (2016.08); *A23L 33/10* (2016.08); *A23L 33/135* (2016.08); *A61K 8/73* (2013.01); *A61K 31/715* (2013.01); *A61Q 19/00* (2013.01); *C12P 19/04* (2013.01); *A23V 2002/00* (2013.01); *A23Y 2260/35* (2013.01); *A61K 35/74* (2013.01)

(58) Field of Classification Search
CPC ........ C08B 37/00; A61K 31/715; A61K 8/73; A61Q 19/00; C12P 19/04; A23L 1/30; A23K 20/163; A23V 2002/00
USPC .................... 536/123.1; 435/252.9
See application file for complete search history.

(56) References Cited

U.S. PATENT DOCUMENTS

| | | | | |
|---|---|---|---|---|
| 8,158,403 | B2* | 4/2012 | Miura ...................... | A23C 9/12 |
| | | | | 426/34 |
| 9,572,844 | B2* | 2/2017 | Yamamoto ................ | C12R 1/01 |
| 2015/0374762 | A1 | 12/2015 | Yamamoto et al. | |

FOREIGN PATENT DOCUMENTS

| | | |
|---|---|---|
| JP | 2008-201708 A | 9/2008 |
| JP | 2010-130954 A | 6/2010 |
| WO | WO 1999/012416 A1 | 3/1999 |

OTHER PUBLICATIONS

Glossary of medical education terms, Institute of International Medical Education. http://www.iime.org/glossary.htm Accessed in Mar. 2013. (Year: 2013).*
Madhuri et al. Microbial Exopolysaccharides: Biosynthesis and Potential Applications. Orient. J. Chem., vol. 30(3), 1401-1410 (2014) (Year: 2014).*
Sato et al. Dextran from Leuconostoc mesenteroides Augments Immunostimulatory Effects by the Introduction of Phosphate Groups. Journal of Food Protection, vol. 67, No. 8, 2004, pp. 1719-1724. (Year: 2004).*
Matsuzaki et al., "IgA-inducing activity of *Leuconostoc mesenteroides* isolated from green peas," *Annual Meeting of the Society for Biotechnology*, 65: 207, abstract 3P-078 (Aug. 25, 2013).
Matsuzaki et al., "Immunomodulating activity of exopolysaccharide-producing *Leuconostoc mesenteroides* strain NTM048," *Journal of Japan Society for Lactic Acid Bacteria*, 25(2): 129, abstract 18-7 (Jul. 5, 2014).
Matsuzaki et al., "Immunomodulating activity of exopolysaccharide-producing *Leuconostoc mesenteroides* strain NTM048 from green peas," *Annual Meeting of the Japan Society for Biosciences, Biotechnology, and Agrochemistry*, Lecture No. 3B06a17 (Mar. 5, 2014).
Matsuzaki et al., "Immunomodulating activity of exopolysaccharide-producing *Leuconostoc mesenteroides* strain NTM048 from green peas," *Journal of Applied Microbiology*, 116(4): 980-989 (2014).
Matsuzaki et al., "Properties of lactic acid bacteria isolated from fresh vegetables and pickles," *Annual Meeting of the Japan Society for Biosciences, Biotechnology, and Agrochemistry*, Lecture No. 3A25a08 (Mar. 5, 2013).
Montersino et al., "Evaluation of Exopolysaccharide Production by *Leuconostoc mesenteroides* Strains Isolated from Wine," *Journal of Food Science*, 73(4): M196-M199 (2008).

(Continued)

*Primary Examiner* — Yih-Horng Shiao
(74) *Attorney, Agent, or Firm* — Leydig, Voit & Mayer, Ltd.

(57) ABSTRACT

Provided are exopolysaccharide produced by novel lactic acid bacteria having an IgA production promoting ability, a production method of the exopolysaccharide, a composition containing the exopolysaccharide, and the like.

6 Claims, 6 Drawing Sheets
Specification includes a Sequence Listing.

(56) References Cited

OTHER PUBLICATIONS

Japanese Patent Office, International Search Report in International Patent Application No. PCT/JP2014/074725 (dated Dec. 22, 2014).
Krieg, "Procaryotic Domains," *Bergey's Manual of Systematic Bacteriology*, Second Edition, vol. One ("The *Archaea* and the Deeply Branching and Phototrophic *Bacteria*"), pp. 21-25 (Springer-Verlag, New York, 2001).
Japan Society for Lactic Acid Bacteria, "Structure and Physiology of Lactic Acid Bacteria and Bifidobacteria," *Science of Lactic Acid Bacteria and Bifidobacteria*, Chapter 2, pp. 104-105 (Kyoto University Press, Kyoto, Japan, 2010).

\* cited by examiner

IgA-inducing activity of EPS
n = 6; *P < 0.05, ***P < 0.001

Items indicated with different letters (i. e., a, b) were signifiantly different ($P < 0.001$).

EXOPOLYSACCHARIDE PRODUCED BY LACTIC ACID BACTERIUM

CROSS-REFERENCE TO RELATED APPLICATIONS

This patent application is the U.S. national phase of International Patent Application No. PCT/JP2014/074725, filed Sep. 18, 2014, which claims the benefit of Japanese Patent Application No. 2013-194656, filed on Sep. 19, 2013, which are incorporated by reference in their entireties herein.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 2,365 bytes ASCII (Text) file named "723688SequenceListing.txt," created Mar. 17, 2016.

TECHNICAL FIELD

The present invention relates to exopolysaccharide (also referred to as EPS) produced by *Leuconostoc mesenteroides*, particularly, *Leuconostoc mesenteroides* NTM048 strain deposited under accession No. NITE BP-1519, a production method of said EPS, a composition containing said EPS, and the like.

BACKGROUND ART

The intestinal immune organ is generically referred to as gut-associated lymphatic tissue (GALT), and mainly constituted of Peyer's patch, mesenteric lymph node and intestinal epithelium. Foreign substances (antigen) such as pathogens and the like that invaded the intestine are incorporated into M cells of Peyer's patch, and presented to T cells by antigen presenting cells such as dendritic cell and the like present in Peyer's patch. Simultaneously, B cells also recognize the antigen, and class switching from IgM$^+$ B cells to IgA$^+$ B cells occurs by cytokine stimulation to finally become plasma cells that secrete immunoglobulin A (hereinafter to be referred to as "IgA").

The number of intestine-specific IgA producing cells is about 70-80% of the plasma cells present in the whole body, and IgA secreted from the plasma cells afford infection defense such as inhibition of attachment of pathogens to the mucosal epithelial cells, neutralization of toxins and enzymes produced from pathogens by IgA binding thereto and the like. Therefore, it is highly important to activate intestinal immunity by IgA production to maintain balance of the immunity.

In recent years, the number of patients having allergic diseases is rapidly increasing. Such patients tend to show a decrease in the intestinal mucosal immunity, and therefore, the enhancement (development) of intestinal mucosal immunity is considered to highly possibility lead to the prophylaxis thereof.

As bacteria having an IgA production promoting ability and capable of enhancing intestinal immunity, *Lactobacillus plantarum* AYA strain (patent document 1), *Lactobacillus gasseri* strain (patent document 2) and the like have been reported.

Lactic acid bacteria are isolated from various plants such as raw vegetable, pickles and the like and added to foods, drinks and the like as a probiotic. However, since reports of lactobacillus having an IgA production promoting ability and capable of activating the intestinal immunity are limited to the above-mentioned documents and the like, provision of new lactic acid bacteria having a high IgA production promoting ability has been desired.

DOCUMENT LIST

Patent Documents

Patent Document 1: JP-A-2008-201708
Patent Document 2: JP-A-2010-130954

SUMMARY OF THE INVENTION

Problems to be Solved by the Invention

The present inventors have conducted intensive studies in an attempt to solve the aforementioned problems and found a strain (NTM048) superior in IgA production promoting ability, and identified that the strain is new lactic acid bacteria (*Leuconostoc mesenteroides*) belonging to the genus *Leuconostoc*.

During the analysis process of NTM048 strain, the present inventors have newly found that NTM048 strain produces exopolysaccharide. Exopolysaccharide is also called extracellular polysaccharide, and some exopolysaccharides produced by microorganisms are known to have a useful action. Therefore, the present invention aims to provide a strain of *Leuconostoc mesenteroides*, more preferably, exopolysaccharide produced by NTM048 strain, a production method of the exopolysaccharide, a composition containing the exopolysaccharide and the like.

Means of Solving the Problems

The present inventors have conducted intensive studies in an attempt to solve the above-mentioned problems and found that exopolysaccharide is secreted in the culture supernatant of NTM048 strain. Furthermore, they have extracted and purified exopolysaccharide and found that it has higher IgA production promoting activity than exopolysaccharide produced by known lactic acid bacteria, which resulted in the completion of the present invention.

Therefore, the present invention provides the following.

[1] Exopolysaccharide produced from *Leuconostoc mesenteroides* NTM048 strain deposited under accession No. NITE BP-1519, or a mutant strain thereof.

[2] A production method of exopolysaccharide, comprising a step of culturing a strain of *Leuconostoc mesenteroides* capable of producing exopolysaccharide.

[3] The method of [2], wherein the *Leuconostoc mesenteroides* is the strain of [1].

[4] The method of [2] or [3], further comprising a step of separating the supernatant of the cultured strain and purifying exopolysaccharide from the supernatant.

[5] An exopolysaccharide obtained by the method of any one of [2]-[4].

[6] A composition comprising the exopolysaccharide of [1] or [5].

[7] The composition of [6], which is a pharmaceutical product.

[8] The composition of [6], which is a food.
[9] The composition of [6], which is a cosmetic.
[10] The composition of [6], which is a feed.

Effect of the Invention

In the present invention, it has been clarified that lactic acid bacteria NTM048 strain newly isolated from pea have an IgA production promoting ability and the strain produces exopolysaccharide. Said exopolysaccharide has a higher IgA production promoting activity than exopolysaccharides produced from known lactic acid bacteria, and can be used in various fields such as food, pharmaceutical product, cosmetic, feed and the like, and therefore, the present invention is industrially extremely useful.

DESCRIPTION OF EMBODIMENTS

Figure 1:
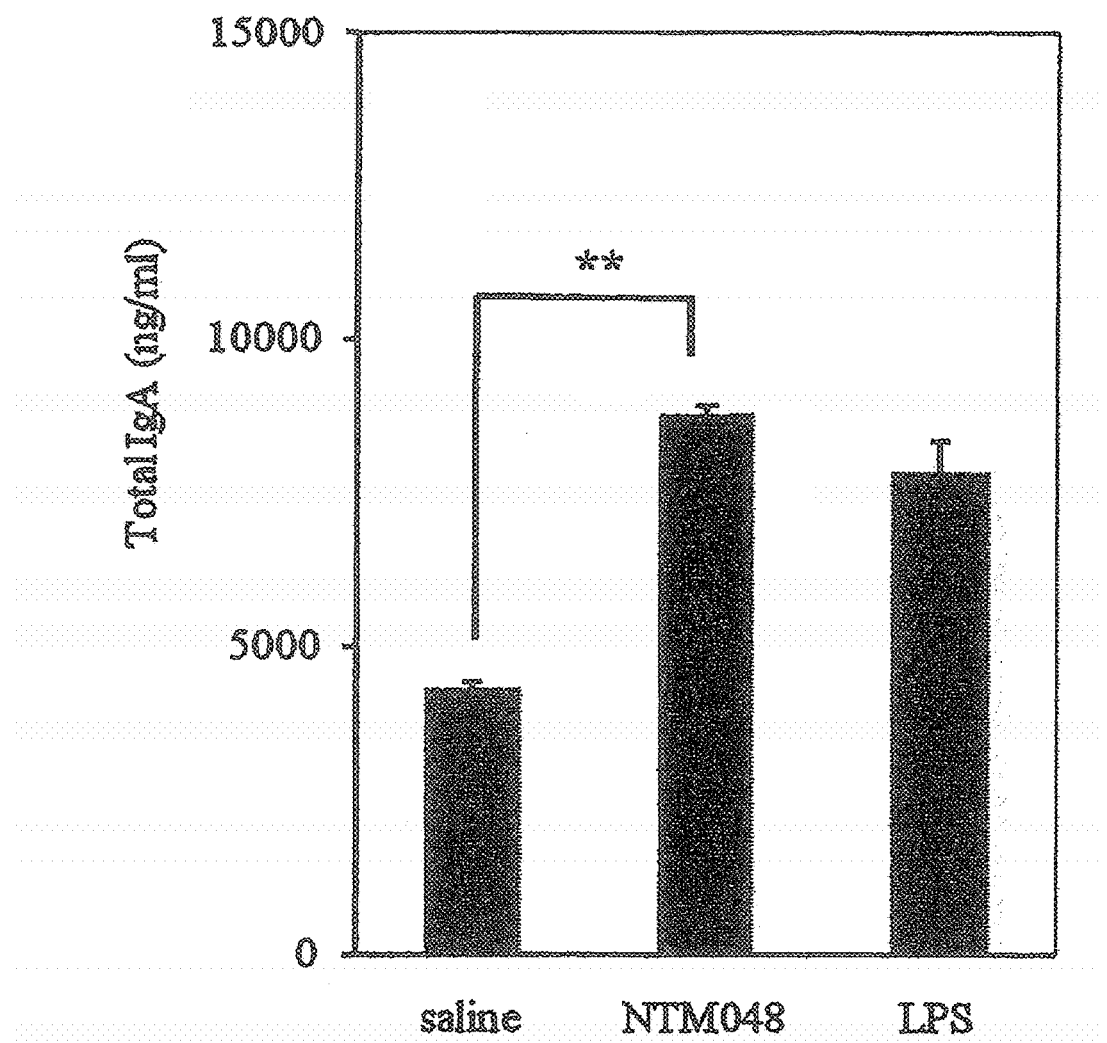
FIG. 1 shows the results of IgA production inducing ability of lactic acid bacteria NTM048 strain isolated in the present invention. In the Figure, the vertical axis shows the total IgA (ng/mL), the horizontal axis shows a negative control (saline), NTM048 strain and a positive control (LPS), and the data shows the mean±standard error (SE) of 6 different experiments. **$P<0.01$

The present invention is explained in detail in the following. The present invention provides exopolysaccharides produced by a strain of Leuconostoc mesenteroides, more preferably, NTM048 strain or a mutant strain thereof, a production method of the exopolysaccharide, a composition containing the exopolysaccharide and the like.

(NTM048 Strain)

In the present invention, new lactic acid bacteria (NTM048 strain) were isolated from pea by the following method. The screening method and the bacteriological properties of NTM048 strain are as follows.

1. Screening
(1) Origin
   pea
(2) Screening Method
   Using a mouse Peyer's patch cell, screening was performed with enhancement of the IgA production as an index.
2. Identification of lactic acid bacteria
(1) Leuconostoc mesenteroides NTM048 strain
(2) Visual characteristics
   (2-1) White Circular Colony on MRS Agar Medium.
   (2-2) Microscopic Characteristics: Coccus, No Motility, Spore is Not Formed.
(3) Growth temperature
   Grows well at 30 -37° C.
(4) Physiological, biochemical characteristics
   Gram staining: positive
   Sugar assimilability is shown in Table 1.

TABLE 1

| 0 | control | − |
|---|---|---|
| 1 | glycerol | − |
| 2 | erythritol | − |
| 3 | D-arabinose | − |
| 4 | L-arabinose | + |
| 5 | ribose | + |
| 6 | D-xylose | + |
| 7 | L-xylose | − |
| 8 | adonitol | − |
| 9 | β-methyl-D-xyloside | − |
| 10 | galactose | + |
| 11 | glucose | + |
| 12 | fructose | + |
| 13 | mannose | + |
| 14 | sorbose | − |
| 15 | rhamnose | − |
| 16 | dulcitol | − |
| 17 | inositol | − |
| 18 | mannitol | + |
| 19 | sorbitol | − |
| 20 | α-methyl-D-mannoside | − |
| 21 | α-methyl-D-glucoside | + |
| 22 | N-acetyl-glucosamine | + |
| 23 | amygdalin | + |
| 24 | arbutin | + |
| 25 | esculin | + |
| 26 | salicin | + |
| 27 | cellobiose | + |
| 28 | maltose | + |
| 29 | lactose | − |
| 30 | melibiose | + |
| 31 | saccharose | + |
| 32 | trehalose | + |
| 33 | inulin | − |
| 34 | melezitose | − |
| 35 | raffinose | + |
| 36 | starch | − |
| 37 | glycogen | − |
| 38 | xylitol | − |
| 39 | gentiobiose | + |
| 40 | D-turanose | + |
| 41 | D-lyxose | − |
| 42 | D-tagatose | − |
| 43 | D-fucose | − |
| 44 | L-fucose | − |
| 45 | D-arabitol | − |
| 46 | L-arabitol | − |
| 47 | gluconate | + |
| 48 | 2-keto-gluconate | − |
| 49 | 5-keto-gluconate | + |

+: positive,
−: negative

As chemical taxonomic properties, moreover, about 1.5 kb 16S rRNA is shown in SEQ ID NO: 1.

From the various properties above and in light of Bergey's Manual of Systematic Bacteriology, this strain was identified as a strain belonging to *Leuconostoc mesenteroides*, and named *Leuconostoc mesenteroides* NTM048. NTM048 strain was deposited on Jan. 25, 2013 at Incorporated Administrative Agency National Institute of Technology and Evaluation Patent Microorganisms Depositary, 2-5-8 Kazusakamatari, Kisarazu-shi, Chiba, Japan. The accession No. is NITE BP-1519.

The strain of the present invention also includes not only the above-mentioned NTM048 strain, but also a mutant of the strain, which shows, at least in the gut-associated lymphatic tissue of mammals, an IgA production promoting capacity etc. equal to or not less than that of NTM048 strain. The mutant more preferably shows an IgA production promoting action in other organ and tissues (e.g., lung, bronchoalveolus, plasma etc.), and a helper T cell increasing action in the spleen, bone marrow, blood and the like, which are equal to or not less than those of NTM048 strain. Examples of a method of introducing mutation include, but are not limited to, a method by a chemical substance treatment such as a nitroso compound (nitrosoamine, nitrosoguanidine etc.), an alkylating agent (EMS; ethyl methanesulfonate), UV irradiation, radiation irradiation and the like. Whether the obtained mutant strain has an IgA production promoting action in the gut-associated lymphatic tissues, which is equal to or not less than that of NTM048 strain, can be detected by measuring the IgA production promoting activity of the mutant strain according to a method similar to the method used for screening the above-mentioned NTM048, and comparing same with the activity of NTM048 strain.

A strain of *Leuconostoc mesenteroides*, more preferably, NTM048 strain and a mutant thereof can be cultivated using a medium for lactic acid bacteria culture (solid medium, liquid medium etc.) such as the aforementioned MRS medium and the like.

In one embodiment, a strain of *Leuconostoc mesenteroides*, more preferably, NTM048 strain or a mutant thereof can be cultured in a suitable medium under conditions permitting formation of EPS. The composition of the suitable medium is not particularly limited as long as EPS is produced, and as a carbon source, for example, sucrose, galactose, xylose, glucose, sorbitol, trehalose, lactose, fructose, maltose, or a mixture of these can be used. In one embodiment, culture can be performed using a medium containing sucrose, bactopeptone, yeast extract, $K_2HPO_4$, $MnCl_2.H_2O$, NaCl, $CaCl_2$ and the like as the composition.

The medium may contain various vitamins (vitamin A, vitamin B1, vitamin B2, vitamin B6, vitamin C, vitamin D, vitamin E etc., and derivatives thereof), various amino acids (including natural amino acid and synthetic amino acid), nucleic acid bases (purine, pyrimidine), inorganic salts ($MgSO_4$, $MnSO_4$, $FeSO_4$, NaCl etc.) and the like as necessary. They are not particularly limited as long as exopolysaccharide is produced, and they may be added in combination to the medium.

The strain of *Leuconostoc mesenteroides*, more preferably, NTM048 strain or a mutant thereof, can be prepared by culturing at a culture temperature of 30-37° C., more preferably 35-37° C., for a culture period of 16 hr-3 days, more preferably 1-2 days, at pH 3-8, more preferably pH 4-7.

The processed bacteria of the strain of the present invention includes a culture medium obtained by the aforementioned method, and/or wet bacteria obtained by treating the culture medium by a method known per se, for example, centrifugation, filtration, magnetic separation and the like, or a washed product thereof (washing with sterilization water, PBS and the like is possible), freeze-dry powder thereof, heat-killed bacteria thereof, dry-killed bacteria thereof, chemical-killed bacteria thereof, bacterial disrupture products such as bacterial wall thereof and the like, an extract thereof and the like.

The processed bacteria of the strain of the present invention also include processed bacteria obtained by inoculating a strain of *Leuconostoc mesenteroides*, more preferably, NTM048 strain or its mutant itself to dairy product, cereal, processed food and the like and fermenting same.

(Exopolysaccharide)

Exopolysaccharide is polysaccharides produced by a strain, and can be classified into homopolysaccharides and heteropolysaccharides. Homopolysaccharide is constituted solely of a single type monosaccharide. Examples thereof include, but are not limited to, α-glucan, β-glucan, galactan and the like. Heteropolysaccharide is constituted of two or more kinds of different repeat units of monosaccharide. Examples of the kind of monosaccharide constituting the repeat units include, but are not limited to, glucose, fructose, galactose, rhamnose, acetylglucosamine, acetylgalactosamine, fucose, glucuronic acid, nonsugar substituents (e.g., acetyl group, glycerol etc.) and the like.

The structure of exopolysaccharide can be analyzed by methods such as NMR analysis, methylation analysis and the like.

The exopolysaccharide of the present invention can be produced by culturing a strain of *Leuconostoc mesenteroides*, more preferably, NTM048 strain or a variant thereof.

While a method of separating exopolysaccharide from a culture medium is not particularly limited as long as exopolysaccharide is obtained, a culture medium can be separated by centrifugation and the like into supernatant and cells, an acid (e.g., trichloroacetic acid, perchloric acid etc.) or an organic solvent (e.g., acetone, methanol, ethanol etc.) is added to the supernatant to remove proteins, alcohol (e.g., ethanol, isopropanol etc.) is further added to precipitate and recover exopolysaccharide. The precipitate may be further purified (e.g., dialysis etc.). The aforementioned separation method can be appropriately adjusted according to culture medium, culture conditions and the like.

The average molecular weight of exopolysaccharide obtained by culturing NTM048 strain of the present invention and separating same can be determined by a known method. For example, a relative molecular weight determination method by GPC liquid chromatography or GFC liquid chromatography and the like can be used. As shown in the below-mentioned Examples, the molecular weight of the exopolysaccharide of the present invention is 30,000-50,000.

(Composition)

The present invention provides a composition containing exopolysaccharide produced by a strain of *Leuconostoc mesenteroides*, more preferably, NTM048 strain or a mutant thereof. The composition may further contain a pharmaceutically acceptable carrier.

The pharmaceutically acceptable carrier refers to a carrier that does not cause an undesirable reaction such as allergic reaction and the like in a subject when administered to the subject. Examples thereof include, but are not limited to, excipient, stabilizer, chelating agent, diluent, gellant, solvent, emulsifier, suspension, decomposing agent, binder, preservative, lubricant, and those similar thereto.

The present invention also provides the aforementioned composition as a pharmaceutical product, food, cosmetic or feed.

The pharmaceutical product of the present invention can be used as an intestinal immunity stimulant, an antiallergic agent, an antivirus agent and the like.

The intestinal immunoactivity refers to an action to promote IgA production in the intestine-related lymphoid tissues. In some cases, it also includes an IgA production regulating action.

The pharmaceutical product of the present invention can be used for the prophylaxis or treatment of diseases relating to the intestinal immunity, allergy, virus infection and the like by administration to human or animals other than human (e.g., dog, cat, mouse, rat, hamster, guinea pig, rabbit, swine, bovine, chicken, parakeet, hill myna, goat, horse, sheep, monkey etc.).

The intestinal immunity stimulant can be applied to diseases relating to the intestinal immunity. Examples of the diseases relating to intestinal immunity include, but are not limited to, food (buckwheat, rice, wheat, egg, milk, peanut, fruits such as orange, apple, kiwi fruit and the like, crustaceans such as shrimp, crab and the like, shell and fish etc.) allergy, pollen (cedar, rice, hogweed, tall goldenrod, artemisia, Japanese white birch, timothy grass, orchard grass etc.) allergy, allergy to house dust, chemical substance, metal and the like, infections (bacterium infections such as *Staphylococcus aureus, Salmonella,* cholera, pathogenic *Escherichia coli, streptococcus mutans, clostridium,* dysentery *bacillus* and the like, virus infection such as influenza virus, rotavirus, norovirus, herpes virus and the like, parasitic insect infection, protozoa infection etc.), inflammatory bowel disease (Crohn's disease, ulcerative colitis etc.), autoimmune disease (organ-specific autoimmune disease and systemic autoimmune disease), functional degradation of intestinal immunity due to stress and the like.

Allergy means excessive immune reaction against particular antigen. Examples of the antiallergic agent include, m but are not limited to, application to type I allergy (food allergy, pollinosis, allergic rhinitis, bronchial asthma, atopic dermatitis etc.), type II allergy (malignant anemia, rheumatic fever, Goodpasture's syndrome, *myasthenia gravis,* chronic thyroiditis etc.), type III allergy (serum sickness, systemic *lupus erythematosus* (*lupus nephritis*), acute glomerulonephritis, rheumatoid arthritis, hypersensitivity pneumonitis, rheumatic pneumonia etc.) and the like.

Examples of the antiviral agent include, but are not limited to, application to infections with influenza virus, AIDS virus and the like.

The dosage form of the pharmaceutical product includes dispersion, granule, pill, soft capsule, hard capsules, tablet, chewable tablet, quick-integrating tablet, syrup, liquid, suspension, suppository, ointment, cream, gel, adhesive, inhalant, injection and the like. A preparation thereof is prepared according to a conventional method.

For administration in the form of an injection, intravenous, intraperitoneal, intramuscular, subcutaneous, transdermal, intraarticular, intrasynovial, intrathecal, intraperiosteum, sublingual, oral administrations and the like are preferable, and intravenous administration or intraperitoneal administration is particularly preferable. The intravenous administration may be any of drip administration and bolus administration.

While the dose of the pharmaceutical product of the present invention varies depending on the subject of administration, target disease, symptom, administration route and the like, for example, a daily dose of the exopolysaccharide of the present invention is generally 0.5 µg-10 g, preferably 5 µg-5 g, more preferably 50 µg-1 g, which can be administered orally or parenterally. Plural divided portions may be administered per day. When the condition is particularly serious, the dose may be increased according to the symptom.

As another embodiment of the pharmaceutical product of the present invention, the present invention also provides a lactic acid bacteria agent, an intestinal immunity stimulant, an antiallergic agent, an antiviral agent and the like, containing, as an active ingredient, a strain of *Leuconostoc mesenteroides,* more preferably, NTM048 strain (also including mutant) or processed bacteria, and a pharmaceutically acceptable carrier (excipient, binder, disintegrant, lubricant etc.).

The aforementioned lactic acid bacteria agent, intestinal immunity stimulant, antiallergic agent, antiviral agent and the like can be used alone. Alternatively, they can also be used in combination with other lactic acid bacteria, lactic acid bacteria preparation, other microorganism, or microorganism preparation.

Examples of other lactic acid bacteria include, but are not limited to, lactic acid bacteria belonging to the genus *Lactobacillus,* the genus *Streptococcus,* the genus *Leuconostoc,* the genus *Pediococcus,* the genus *Lactococcus,* the genus *Enterococcus,* the genus *Bifidobacterium* and the like, and examples of the lactic acid bacteria preparation include, but are not limited to, preparations containing the above-mentioned bacteria.

Examples of other microorganism include, but are not limited to, yeast, the genus bacillus, butyric acid bacteria (*Clostridium butyricum*), fungi such as koji bacteria and the like, and the like, and examples of the microorganism preparation include, but are not limited to, preparations containing the above-mentioned microorganisms.

Examples of the additives include animal and plant oils such as soybean oil, safflower oil, olive oil, germ oil, sunflower oil, beef tallow, sardine oil and the like, polyvalent alcohols such as polyethylene glycol, propylene glycol, glycerol, sorbitol and the like, surfactants such as sorbitan fatty acid ester, sucrose fatty acid ester, glycerin fatty acid ester, polyglycerol fatty acid ester and the like, purified water, lactose, starch, crystalline cellulose, D-mannitol, lecithin, gum arabic, sorbitol solution, carbohydrate solution and the like. Examples of the binder include hydroxypropylmethylcellulose, hydroxypropylcellulose, gelatin, pregelatinized starch, polyvinylpyrrolidone, polyvinyl alcohol and the like. Examples of the disintegrant include carmellose calcium, carmellose sodium, croscarmellose sodium, crospovidone, low-substituted hydroxypropylcellulose, cornstarch and the like. Examples of the lubricant include talc, hydrogenated vegetable oil, waxes, light anhydrous silicic acid and the like derived from naturally occurring substance and derivatives thereof, stearic acid, magnesium stearate, calcium stearate, aluminum stearate and the like.

The above-mentioned pharmaceutical products can further contain a sweetener, a colorant, a pH adjuster, a flavor, various amino acids and the like. Also, tablet and granule may be coated by a well-known method. A liquid preparation may be dissolved or suspended in water or other suitable medium when in use.

As the number of bacterial NTM048 strains or mutant strains thereof contained in the above-mentioned pharmaceutical products, the daily ingestion amount is not less than $10^4$ colony forming units (hereinafter to be referred to as cfu) and not more than $10^{12}$ cfu, preferably not less than $10^6$ cfu and not more than $10^9$ cfu.

The food of the present invention is not particularly limited as long as it permits oral ingestion, such as solution, suspension, powder, solid formed article and the like. Specific examples include supplements (dispersion, granule, soft capsule, hard capsule, tablet, chewable tablet, quick-integrating tablet, syrup, liquid etc.), drinks (carbonic acid drinks, lactic acid drinks, sport drinks, fruit juice drinks, vegetable drinks, soymilk drinks, coffee drinks, tea drinks, powder drinks, concentrated drinks, nutrition drinks, alcohol drinks etc.), dairy products (yogurt, butter, cheese, ice cream etc.), confectionery (gummy, jelly, gum, chocolate, cookie, candy, caramel, Japanese confectionery, snack etc.), instant food (instant noodles, retort food, can, microwavable foods, instant soup, miso soups, freeze-dried food etc.), oil, fats and oils food (mayonnaise, dressing, cream, margarine etc.), wheat powder products (bread, pasta, noodle, cake mix, bread crumb etc.), seasoning (sauce, tomato processing seasoning, flavor seasoning, cooking mixture, soup etc.), processed meat products (meat ham, sausage etc.).

The above-mentioned foods can contain, where necessary, various nutrients, various vitamins (vitamin A, vitamin B1, vitamin B2, vitamin B6, vitamin C, vitamin D, vitamin E, vitamin K etc.), various minerals (magnesium, zinc, iron, sodium, potassium, selenium etc.), dietary fiber, dispersing agent, stabilizer such as emulsifier and the like, sweetener, flavor components (citric acid, malic acid etc.), flavor, royal jelly, propolis, Agaricus and the like.

While the daily ingestion amount of the food of the present invention varies depending on the subject that ingests the food, target disease, symptom and the like, for example, a daily ingestion amount of the polysaccharide of the present invention is generally 0.1 mg-10 g, preferably 1 mg-5 g, more preferably 10 mg-1 g, which can be ingested orally. Plural divided portions may be ingested per day. When the condition is particularly serious, the amount may be increased according to the symptom.

Examples of the cosmetic of the present invention include, but are not limited to, cream, gel, skin milk, serum, toner, microemulsion essense, facial mask, foundation, lip rouge, eye shadow, shampoo, conditioner, bathing powder and the like. Furthermore, a flavor and the like may be mixed.

While the daily amount of use of the cosmetic of the present invention varies depending on the use target, target disease, symptom and the like, for example, a daily amount of use of the exopolysaccharide of the present invention is generally 1 µg-30 g, preferably 10 µg-10 g, more preferably 100 µg-1 g. Plural divided portions may be used per day. When the condition is particularly serious, the amount may be increased according to the symptom.

The feed of the present invention is, for example, pet food, stock raising or aquaculture feed additive and the like.

While the daily ingestion amount of the feed of the present invention varies depending on the animal that ingests the feed, target disease, symptom and the like, for example, a daily ingestion amount of the polysaccharide of the present invention is generally 1 µg/kg body weight—0.2 g/kg body weight, preferably 10 µg/kg body weight—0.02 g/kg body weight, more preferably 0.1 mg/kg body weight—2 mg/kg body weight, which can be ingested orally. Plural divided portions may be ingested per day. When the condition is particularly serious, the dose may be increased according to the symptom.

(IgA Production)

In the present invention, the IgA production can be measured by a method known per se. For example, Peyer's patch cell is prepared by the method using collagenase as shown in the below-mentioned Examples and the like, the Peyer's patch cell is cultured in the presence of lactic acid bacteria, and the culture supernatant is recovered. The amount of IgA contained in the culture supernatant is measured by a method known per se such as the ELISA method (commercially available IgA measurement kit etc.) and the like. Thereafter, changes in the IgA amount are confirmed by comparing with a control group (e.g., saline as negative control, LPS etc. as positive control).

Peyer's patch cell can be selected irrespective of the kind thereof such as mouse, rat, human and the like and the production method thereof is not limited to the above-mentioned methods and those of ordinary skill in the art can appropriately select them as necessary. Alternatively, to measure IgA production inducing activity in vivo, a biological sample (blood, feces etc.) can be collected from an individual (mouse, rat, human etc. irrespective of the kind), and changes in the IgA amount in the sample can be confirmed.

The present invention is explained in more detail in the following by referring to Examples. The Examples are mere exemplifications of the present invention and do not limit the scope of the present invention in any manner.

EXAMPLES

Medium, Reagent and Strain medium: RPMI-10 medium [RPMI 1640 medium (manufactured by Gibco) added with 10% fetal bovine serum], MRS medium (manufactured by Difco)

reagent: collagenase (manufactured by Sigma), DNase (manufactured by Takara), dextran produced by B512F strain (*Leuconostoc mesenteroides*) (manufactured by Sigma)

strain: NTM048 strain [isolated from pea (accession No.: NITE BP-1519, date of deposition: Jan. 25, 2013)], JCM16943 strain (*Leuconostoc mesenteroides* subsp. *cremoris*), JCM6124 strain (*Leuconostoc mesenteroides* subsp. *mesenteroides*) [purchased from RIKEN, Tsukuba, BioResource Center, Japan Collection of Microorganism (JCM)]

Reference Experimental Example 1

Preparation of Peyer's Patch Cell by Production Method Using Collagenase

Small intestine Peyer's patch was isolated from 7-week-old BALE/cA mouse. The Peyer's patch was washed with RPMI-10 medium, transferred to a sterile dish containing 5 mL of IEC-dissociating solution (25 mM HEPES, 5 mM EDTA, 1 mM DTT in RPMI-10), and incubated in a $CO_2$ incubator at 37° C. for 45 min. After pipetting well, the cells were transferred to a sterile dish containing 5 mL of EDTA solution (5 mM EDTA in RPMI-10), and incubated in a $CO_2$ incubator at 37° C. for 5 min. After further pipetting well, the Peyer's patch was transferred to a 50 mL tube containing 5 mL of digestion solution (400 U/mL collagenase, 30 U/mL DNase in RPMI-10) and a stirrer, and incubated with stirring at 37° C. for 30 min. After completion of enzyme decomposition, Peyer's patch cells suspended in the medium were cloudy. They were centrifuged (1400 rpm, for 7 min, 4° C.), and 4 mL of the supernatant was removed by suction. A suspension (1 mL) of the Peyer's patch cells was passed through a 40 pm cell strainer, centrifuged (1400 rpm, for 7 min, 4° C.), the supernatant was removed by suction and suspended in 1 mL of RPMI-10 medium. The cells were counted, and used for the measurement of immune function activity.

Reference Experimental Example 2

Measurement of IgA Production Amount

About 200 strains of lactic acid bacteria isolated from various raw vegetables and pickles were investigated for the IgA production promoting ability by using mouse small intestine Peyer's patch cells.

The concentration of Peyer's patch cells obtained by the aforementioned production method using collagenase was adjusted to $2.5 \times 10^5$ cells/mL in a CD3 antibody-coated 96 well plate (manufactured by BD Biosciences). To the suspension of Peyer's patch cells was added an equal amount of lactic acid bacteria having a concentration adjusted to 10 μg/mL with saline after liquid culture in MRS medium, and the mixture was reacted at 37° C. under 5% $CO_2$ anaerobic conditions for 5 days, and the total IgA amount produced from the Peyer's patch was measured using Mouse IgA ELISA Quantitation Set (manufactured by BETHYL). The results of lactic acid bacteria NTM048 strain are shown in FIG. 1.

Two strains of lactic acid bacteria (NTM047, NTM048) having a significantly high IgA production promoting ability were selected. The both NTM047, NTM048 strains were heat treated at 70° C. for 30 min, and the obtained killed bacteria were similarly examined for the IgA production promoting ability by using Peyer's patch cells. As a result, the both strains were confirmed to have an IgA production promoting ability like that of living bacteria. The results suggest that IgA production inducing substances by NTM047 strain and NTM048 strain are bacterial walls or extra-bacterial components. Furthermore, species identification was tried by 16S rDNA sequence analysis. As a result, the both strains were clarified to be the same strains.

Reference Experimental Example 3

Comparison with Type Strain

Figure 2:
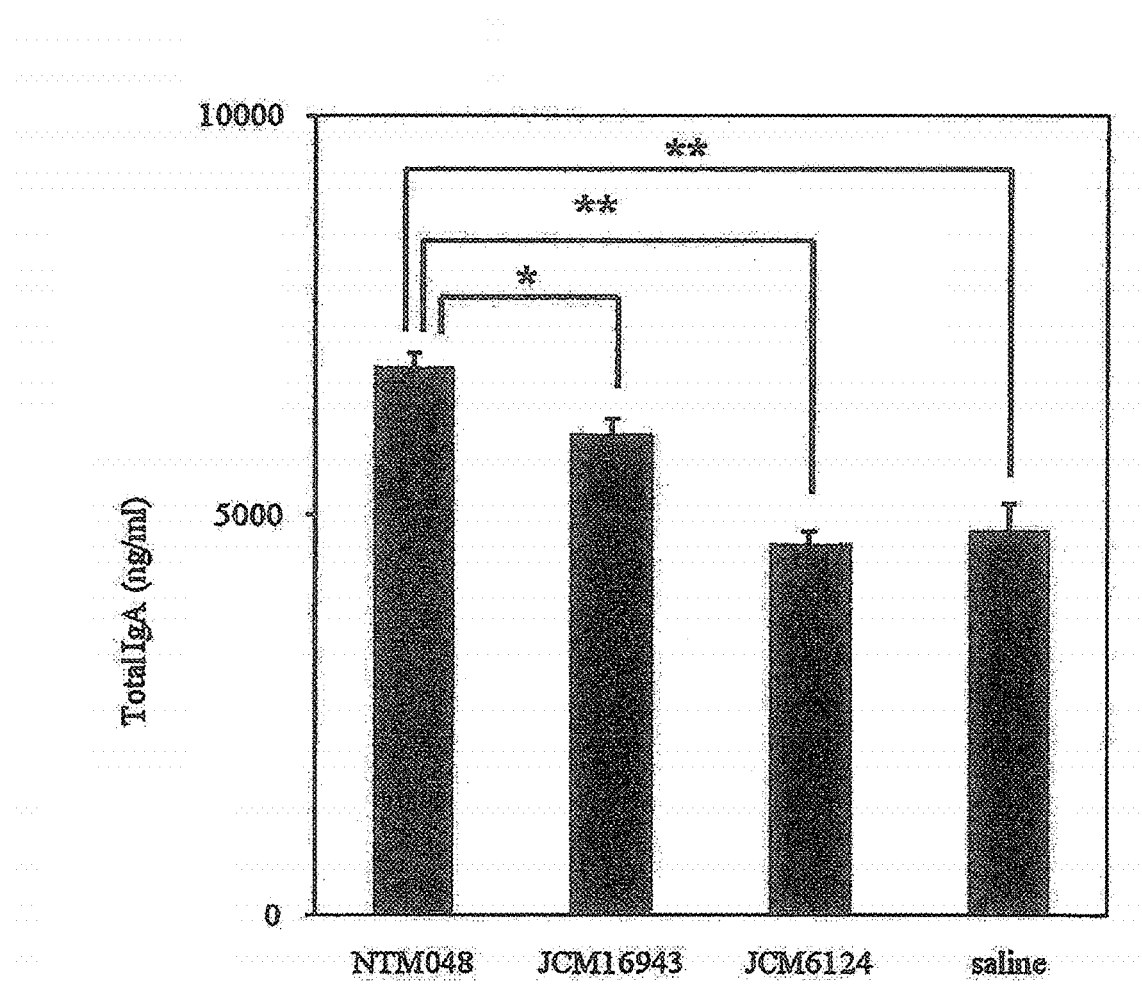
FIG. 2 shows the comparison results of the IgA production inducing activity of NTM048 strain and other Leuconostoc mesenteroides strains. In the Figure, the vertical axis shows the total IgA (ng/mL), the horizontal axis shows various strains, a negative control (saline), and the data shows the mean±standard error (SE) of 6 different experiments. *$P<0.05$, **$P<0.01$

By a method similar to that of Reference Experimental Example 2, IgA production inducing activity in vitro was compared between NTM048 strain, and JCM16943 strain and JCM6124 strain by using Peyer's patch cells. The results are shown in FIG. 2.

NTM048 strain was confirmed to highly induce IgA production as compared to other strains of *Leuconostoc mesenteroides*.

Reference Experimental Example 4

Confirmation of IgA Production Inducing Activity in vivo

6-Week-old male BALB/c mice were preliminarily reared (lactic acid bacteria-free feed; AIN-76) for 2 weeks, AIN-76 containing 0, 0.05, 0.5, 5% lactic acid bacteria NTM048 strain was administered to 5 mice in each test group for 2 weeks, the feces was collected on days 0, 7, 14 and IgA amount was confirmed. After collection, the feces was freeze-dried for 6 hr, and suspended at a ratio of feces weight 10 mg/200 μL in an extraction buffer (PBS) containing Protease Inhibitor Cocktail (manufactured by Roche). The suspension was stirred by vortex, ice-cooled for 30 min, centrifuged (15000 rpm, for 10 min, 4° C.), and the total IgA amount extracted into the supernatant was measured by the ELISA method as mentioned above.

Figure 3:
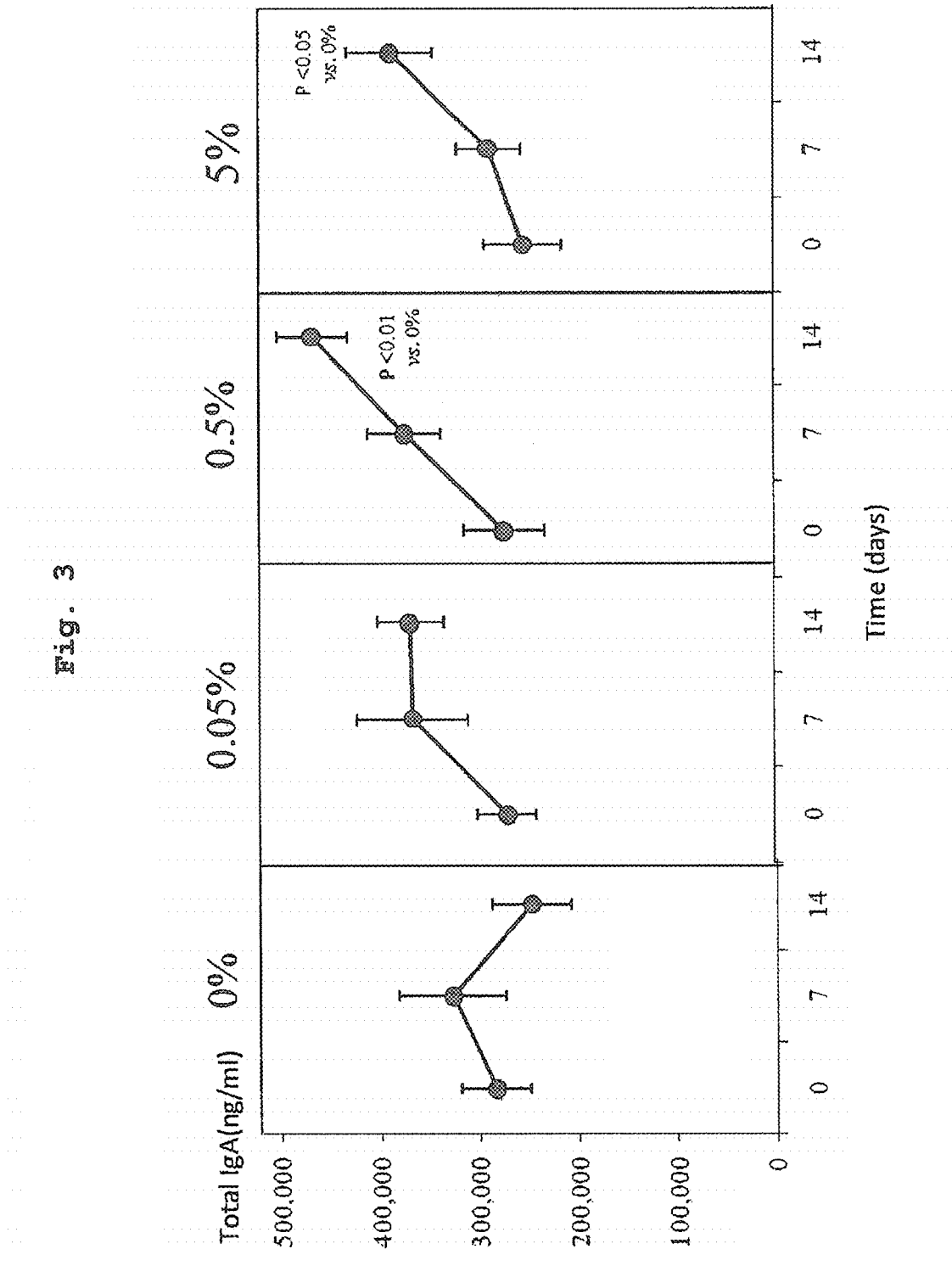
FIG. 3 shows IgA production inducing activity when feeds containing NTM048 strain were orally administered to mouse. In the Figure, the vertical axis shows the total IgA (ng/mL), and the horizontal axis shows the number of days, and the data shows mean±standard error (SE) of an experiment per 5 mice in the test section. *$P<0.05$, **$P<0.01$
Figure 4:
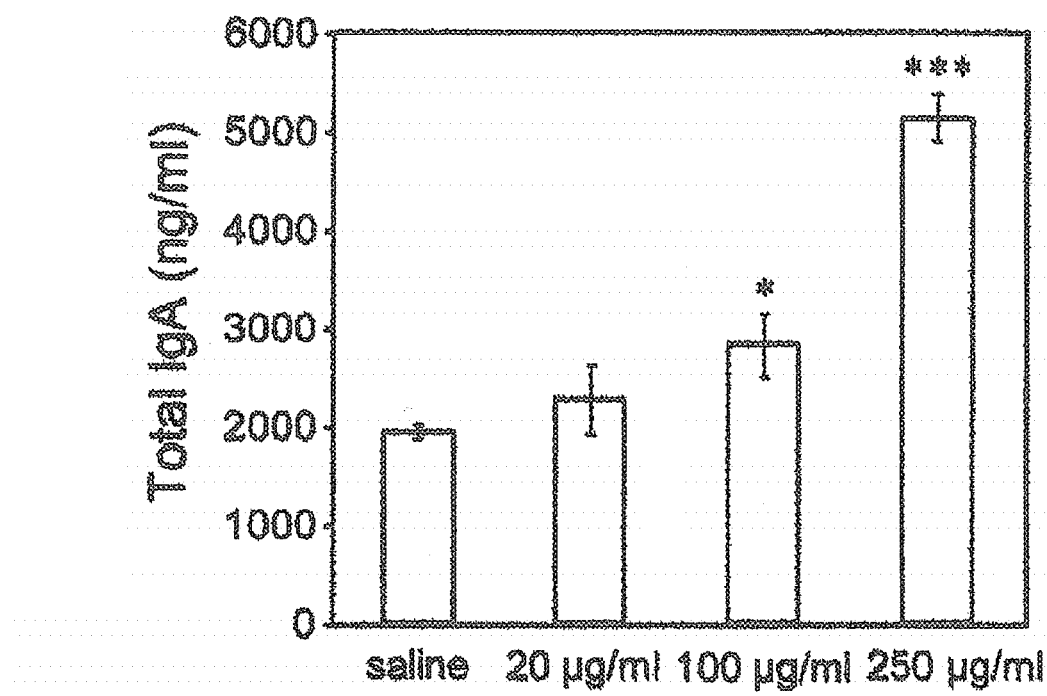
FIG. 4 shows the results of IgA induction by EPS. In the Figure, the vertical axis shows the total IgA (ng/mL), the horizontal axis shows a negative control (saline), and EPS concentrations of 20 μg/mL, 100 μg/mL, 250 μg/mL.

The composition of the feed is shown in Table 2, and the results of IgA production induction are shown in FIG. 3.

TABLE 2

| test group | feed composition (%) bacteria (%) | feed composition (%) bacterial body (%) | feed composition (g) AIN-76 | feed composition (g) bacteria | feed composition (g) dispersing medium | feed composition (g) total | CFU/g (feed) |
|---|---|---|---|---|---|---|---|
| 1 | 0 | 0 | 95 | 0 | 5 | 100 | 0 |
| 2 | 0.05 | 0.0038 | 95 | 0.05 | 4.95 | 100 | $7.1 \times 10^8$ |
| 3 | 0.5 | 0.038 | 95 | 0.5 | 4.5 | 100 | $7.1 \times 10^9$ |
| 4 | 5 | 0.38 | 95 | 5 | 0 | 100 | $7.1 \times 10^{10}$ |

On day 14, the IgA amount increased in all bacteria administration groups, and a significant difference ($P<0.01$, $P<0.05$) was found in 0.5% and 5% NTM048 strain administration mice.

Example 1

Production and Purification Method of Exopolysaccharide (EPS)

EPS was extracted according to the production and purification method for EPS of L. mesenteroides strain (Sarwat, Ul Qader, Aman, &Ahmed, 2008).

NTM048 strain culture medium (500 μL) cultured overnight was added to EPS production medium (50 μL, composition: 15% sucrose, 0.5% bacto-peptone, 0.5% yeast extract, 1.5% $K_2HPO_4$, 0.001% $MnCl_2.O$, 0.001% NaCl, 0.005% $CaCl_2$), cultured at 30° C. for 24 hr and centrifuged, and bacterial body was removed. Cold ethanol in the same amount as the supernatant was added to allow for precipitation, and the mixture was shaken vigorously and centrifuged at 10,000 rpm for 15 min, and the supernatant was removed. This step was repeated twice. The precipitated EPS was dried on calcium chloride for 12 hr. To remove impurity, EPS precipitate was dissolved in distilled water, and cold ethanol in the same amount as the suspension was added again to allow for precipitation. This step was repeated twice. The precipitated EPS was dried on calcium chloride for 12 hr. The EPS was dissolved in saline, and used for the measurement of the IgA production inducing activity.

Example 2

IgA Measurement

Using Peyer's patch cells prepared by a method similar to that of Reference Experimental Example 1, IgA production promoting ability of exopolysaccharide (EPS) produced by and purified from NTM048 strain was studied.

The concentration of Peyer's patch cells obtained by the aforementioned production method of Reference Experimental Example 1 using collagenase was adjusted to $2.5 \times 10^5$ cells/mL in a CD3 antibody-coated 96 well plate (manufactured by BD Biosciences). To the suspension of Peyer's patch cells was added an equal amount of EPS adjusted with saline to concentrations of 20 μg/mL, 100 μg/mL, 250 μg/mL, and the mixtures were reacted at 37° C. under 5% $CO_2$ anaerobic conditions for 5 days, and the total IgA amounts produced from the Peyer's patch cells were measured using Mouse IgA ELISA Quantitation Set (manufactured by BETHYL). The results of exopolysaccharide (EPS) produced by NTM048 strain are shown in FIG. 4.

Example 3

Comparison with EPS Produced by Type Strain

Using Peyer's patch cells prepared by a method similar to that of Reference Experimental Example 1, IgA production promoting ability of exopolysaccharide (EPS) produced by and purified from NTM048 strain, dextran produced by B512F strain, and exopolysaccharide (EPS) produced by and purified from JCM6124 strain was studied. As the dextran produced by B512F strain, a reagent manufactured by Siyma (product No. 31398) was used as exopolysaccharide (EPS). EPS produced by and purified from JCM6124 strain was produced and purified by a method similar to that of Example 1.

Figure 5:
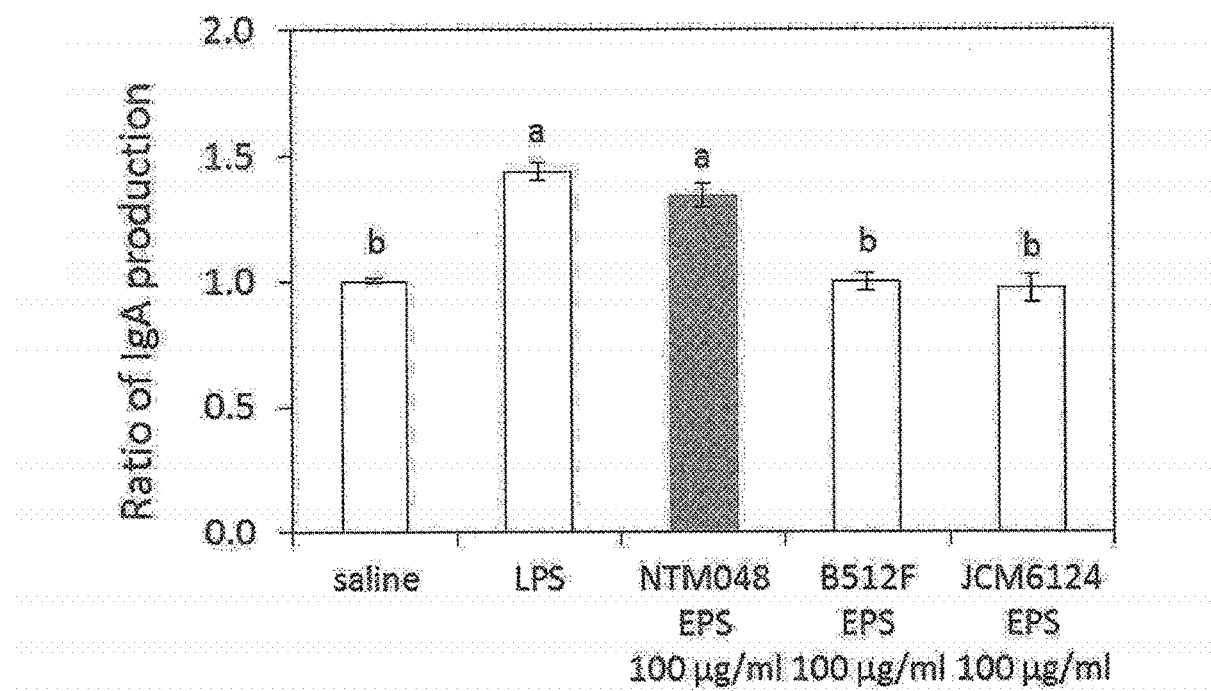
FIG. 5 shows the comparison results of the IgA production inducing activity of EPS produced and purified from each strain. In the Figure, the vertical axis shows the rate of IgA production, and the horizontal axis shows negative control (saline), positive control (LPS), NTM048 strain (EPS), B512F strain (EPS), and JCM6124 strain (EPS).

The concentration of Peyer's patch cells obtained by the production method of Reference Experimental Example 1 using collagenase was adjusted to $2.5 \times 10^5$ cells/mL in a CD3 antibody-coated 96 well plate (manufactured by BD Biosciences). To the suspension of Peyer's patch cells was added an equal amount of EPS having a concentration adjusted with saline to 100 μg/mL, and the mixture was reacted at 37° C. under 5% $CO_2$ anaerobic conditions for 5 days, and the total IgA amount produced was measured using Mouse IgA ELISA Quantitation Set (manufactured by BETHYL). The results of EPS produced by NTM048 strain, dextran produced by B512F strain and JCM6124 strain are shown in FIG. 5. An equal amount of saline as a negative control and an equal amount of lipopolysaccharide (LPS) (manufactured by Sigma) (10 μg/mL) as a positive control were added, and IgA production amount was measured in the same manner as with EPS. EPS produced by NTM048 strain was confirmed to highly induce IgA production as compared to EPS produced by other strain.

Example 4

Molecule Size of Exopolysaccharide (EPS)

Figure 6:
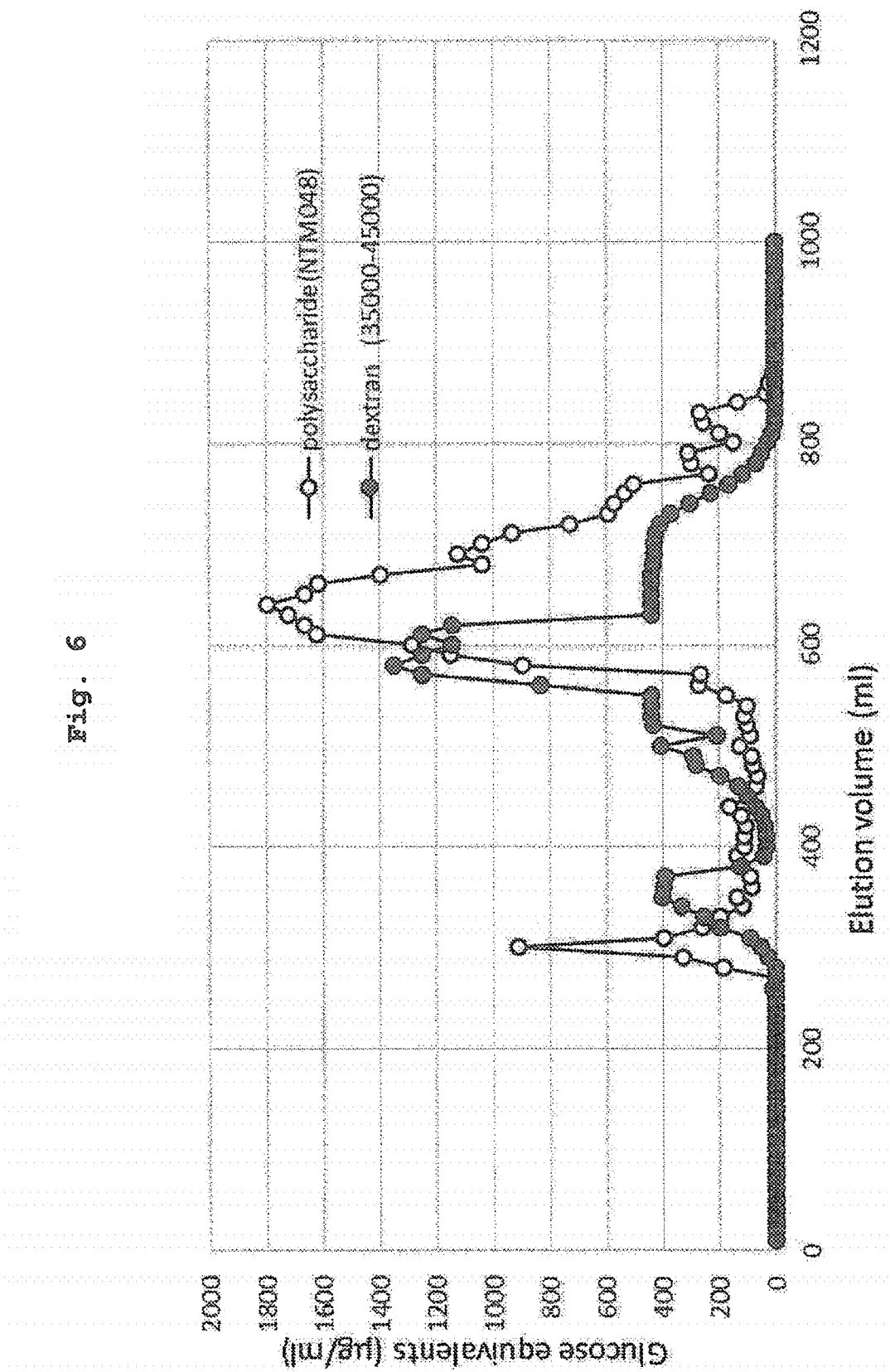
FIG. 6 shows the measurement results of the molecule size of EPS, produced by NTM048 strain, by gel filtration chromatography. In the Figure, the vertical axis shows Glucose equivalents (μg/mL), and the horizontal axis shows Elution Volume (mL).

EPS (20 mg) produced by and purified from NTM048 strain in Example 1 was suspended in ultrapure water (20 mL), and dissolved by ultrasonication for 24 hr. The solution was eluted with ultrapure water at a flow rate of 35 mL/h by gel filtration chromatography using Sepharose CL6B (manufactured by Sigma). The results are shown in FIG. 6. The polysaccharide concentration of each fraction was measured by a phenolsulfuric acid method.

Using dextran D1662 having a molecular weight of 35,000-45,000 (manufactured by Siyma) as a control, the extraction peak was confirmed. As a result, the molecular weight of EPS produced by NTM048 strain was assumed to be 30,000-50,000.

While the present invention has been described with emphasis on preferred embodiments, it is obvious to those skilled in the art that the preferred embodiments can be modified.

The contents disclosed in any publication cited herein, including patents and patent applications, are hereby incorporated in their entireties by reference, to the extent that they have been disclosed herein.

INDUSTRIAL APPLICABILITY

The present invention has clarified that lactic acid bacteria (NTM048 strain) having a high IgA production promoting ability produces exopolysaccharide. Since the exopolysaccharide can be applied to various fields such as pharmaceutical product, food and drink, cosmetic, feed and the like, the present invention is industrially extremely useful.

This application is based on patent application No. 2013-194656 filed in Japan on Sep.19, 2013, the contents of which are incorporated in full herein.

The invention claimed is:

1. A method of stimulating intestinal immunity in a mammal in need thereof, comprising administering to the mammal an effective amount of purified exopolysaccharide produced from *Leuconostoc mesenteroides* NTM048 strain deposited under accession No. NITE BP-1519, or a mutant strain thereof.

2. A method of treating an allergy in a mammal in need thereof, comprising administering to the mammal an effective amount of purified exopolysaccharide produced from *Leuconostoc mesenteroides* NTM048 strain deposited under accession No. NITE BP-1519, or a mutant strain thereof.

3. A method of treating an infection of virus in a mammal in need thereof, comprising administering to the mammal an effective amount of purified exopolysaccharide produced from *Leuconostoc mesenteroides* NTM048 strain deposited under accession No. NITE BP-1519, or a mutant strain thereof.

4. The method of claim 1, wherein an effective amount of the purified exopolysaccharide produced from *Leuconostoc mesenteroides* NTM048 strain deposited under accession No, NITE BP-1519 is administered to the mammal.

5. The method of claim 2, wherein an effective amount of the purified exopolysaccharide produced from *Leuconostoc mesenteroides* NTM048 strain deposited under accession No, NITE BP-1519 is administered to the mammal.

6. The method of claim 3, wherein an effective amount of the purified exopolysaccharide produced from *Leuconostoc mesenteroides* NTM048 strain deposited under accession No, NITE BP-1519 is administered to the mammal.

* * * * *

SEQUENCE LISTING

<160> NUMBER OF SEQ ID NOS: 1

<210> SEQ ID NO 1
<211> LENGTH: 1516
<212> TYPE: DNA
<213> ORGANISM: Leuconostoc mesenteroides subsp. mesenteroides

<400> SEQUENCE: 1

```
agagtttgat cctggctcag gatgaacgct ggcggcgtgc ctaatacatg caagtcgaac      60
gcacagcgaa aggtgcttgc acctttcaag tgagtggcga acgggtgagt aacacgtgga     120
caacctgcct caaggctggg gataacattt ggaaacagat gctaataccg aataaaactt     180
agtgtcgcat gacacaaagt taaaggcgc ttcggcgtca cctagagatg gatccgcggt      240
gcattagtta gttggtgggg taaaggccta ccaagacaat gatgcatagc cgagttgaga     300
gactgatcgg ccacattggg actgagacac ggcccaaact cctacgggag gctgcagtag     360
ggaatcttcc acaatgggcg aaagcctgat ggagcaacgc cgcgtgtgtg atgaaggctt     420
tcgggtcgta aagcactgtt gtatgggaag aacagctaga ataggaaatg attttagttt     480
gacggtacca taccagaaag ggacggctaa atacgtgcca gcagccgcgg taatacgtat     540
gtcccgagcg ttatccggat ttattgggcg taaagcgagc gcagacggtt tattaagtct     600
gatgtgaaag cccggagctc aactccggaa tggcattgga aactggttaa cttgagtgca     660
```

```
gtagaggtaa gtggaactcc atgtgtagcg gtggaatgcg tagatatatg gaagaacacc    720
agtggcgaag gcggcttact ggactgcaac tgacgttgag gctcgaaagt gtgggtagca    780
aacaggatta gataccctgg tagtccacac cgtaaacgat gaacactagg tgttaggagg    840
tttccgcctc ttagtgccga agctaacgca ttaagtgttc cgcctgggga gtacgaccgc    900
aaggttgaaa ctcaaaggaa ttgacgggga cccgcacaag cggtggagca tgtggtttaa    960
ttcgaagcaa cgcgaagaac cttaccaggt cttgacatcc tttgaagctt ttagagatag   1020
aagtgttctc ttcggagaca aagtgacagg tggtgcatgg tcgtcgtcag ctcgtgtcgt   1080
gagatgttgg gttaagtccc gcaacgagcg caacccttat tgttagttgc cagcattcag   1140
atgggcactc tagcgagact gccggtgaca aaccggagga aggcggggac gacgtcagat   1200
catcatgccc cttatgacct gggctacaca cgtgctacaa tggcgtatac aacgagttgc   1260
caacccgcga gggtgagcta atctcttaaa gtacgtctca gttcggattg tagtctgcaa   1320
ctcgactaca tgaagtcgga atcgctagta atcgcggatc agcacgccgc ggtgaatacg   1380
ttcccgggtc ttgtacacac cgcccgtcac accatgggag tttgtaatgc ccaaagccgg   1440
tggcctaacc ttttaggaag gagccgtcta aggcaggaca gatgactggg gtgaagtcgt   1500
aacaaggtaa ccgtaa                                                    1516
```